(12) United States Patent
Sim et al.

(10) Patent No.: US 7,785,823 B2
(45) Date of Patent: Aug. 31, 2010

(54) **METHOD FOR SELECTIVE SEPARATION OF FREE-ASTAXANTHIN FROM GREEN ALGAE *HAEMATOCOCCUS PLUVIALIS***

(75) Inventors: Sang-jun Sim, Seoul (KR); Chang-deok Kang, Seoul (KR)

(73) Assignee: Sungkyunkwan University, Gyeonggi-Do (KR)

( * ) Notice: Subject to any disclaimer, the term of this patent is extended or adjusted under 35 U.S.C. 154(b) by 704 days.

(21) Appl. No.: 11/677,302

(22) Filed: Feb. 21, 2007

(65) Prior Publication Data
US 2007/0196894 A1      Aug. 23, 2007

(30) Foreign Application Priority Data
Feb. 21, 2006    (KR) ...................... 10-2006-0016826

(51) Int. Cl.
*C12P 23/00*     (2006.01)
(52) U.S. Cl. .................. 435/67; 435/171; 435/257.1
(58) Field of Classification Search ........................ None
See application file for complete search history.

(56) References Cited

U.S. PATENT DOCUMENTS
5,453,565 A * 9/1995 Mawson ...................... 435/67

OTHER PUBLICATIONS
Yuan et al., Food Chemistry, vol. 68, pp. 443-448, 2000.*
Hejazi et al. (I), (Trends in Biotechnology, vol. 22, pp. 189-194, 2004.*
Hejazi et al. (II), Biotechnology and Bioengineering, vol. 79, 2002, pp. 29-35.*

* cited by examiner

*Primary Examiner*—Irene Marx
(74) *Attorney, Agent, or Firm*—Hamre, Schumann, Mueller & Larson, P.C.

(57) ABSTRACT

There is provided a method of separating free-astaxanthin selectively from green algae and, more particularly, to a method of separating free-astaxanthin selectively from *Haematococcus pluvialis*, the method comprising: mixing a cell culture containing *Haematococcus pluvialis* with an alkanic solvent and stirring, thereby obtaining an alkanic solvent extract containing astaxanthin material including free-astaxanthin and astaxanthin ester (step 1); and mixing the alkanic solvent extract with an alcohol and stirring, thereby obtaining an alcoholic extract containing free-astaxanthin (step 2).

2 Claims, 4 Drawing Sheets

Drawings

METHOD FOR SELECTIVE SEPARATION OF FREE-ASTAXANTHIN FROM GREEN ALGAE *HAEMATOCOCCUS PLUVIALIS*

CROSS-REFERENCE TO RELATED APPLICATION

This application claims the benefit of Korean Patent Application No. 10-2006-0016826, filed Feb. 21, 2006, the disclosure of which is hereby incorporated herein by reference in its entirety.

BACKGROUND OF THE INVENTION

1. Technical Field

The present invention relates to a method of separating free-astaxanthin selectively from green algae and, more particularly, to a method of separating free-astaxanthin selectively from a green microalgae *Haematococcus pluvialis*.

2. Discussion of Related Art

Red ketocarotenoid astaxanthin is a kind of carotenoid pigment having the same chemical structure as β-carotene, and is an anti-oxidizing material having an ability of removing detrimental activated oxygen that causes aging or a cancer. Astaxanthin has outstandingly higher anti-oxidizing activity than that of an existing anti-oxidizing material since it has a unique molecular structure having one more a hydroxyl group (—OH) and a ketone group (=O) at both end groups compared to β-carotene. The anti-oxidizing activity of astaxanthin is about 500-fold higher than representative anti-oxidizing agent vitamin E, and about 20-fold higher than β-carotene. Due to such high anti-oxidizing activity, astaxanthin is being widely used as a pharmaceutical, a food additive, and a feed additive for an animal and a fry. Further, it is expected that the demand and the application range for astaxanthin be rapidly expanded.

A method of producing astaxanthin includes a chemical synthesis, a method of extracting from shells of the *Crustacea* such as a crab and a shrimp, and a direct synthesis employing microorganism strains *Phaffia rhodozyma* and *Haematococcus pluvialis*.

The astaxanthin synthesized by chemical synthesis has less in vivo absorption rate than that of natural one, has a problem in safety as a food additive, and thus FDA approval was not given to it as a food additive. Only some countries such as Norway, Chile and Canada approve it as a food additive.

Following research results that natural astaxanthin is deposited on a living organism in high concentration compared to synthetic astaxanthin, natural astaxanthin have been produced from byproducts of a shrimp or a crab, however, there is a problem that the natural astaxanthin thus produced is not suitable as an astaxanthin source due to the difficulty in its separation and purification process.

Consequently, biosynthesis through strain cell culture is required for producing natural astaxanthin. Strains that can be used industrially include *P. rhodozyma* and *H. pluvialis*. Green algae *H. pluvialis* has problems of low growth rate, thick cell wall and low cell density, even though it has outstandingly high amount of accumulated astaxanthin compared to yeast *P. rhodozyma*. Therefore, *H. pluvialis* is behind *P. rhodozyma* having high growth rate in preference and industrial applicability, but is deemed to be the most promising strain since 3S, 3S' astaxanthin isomer that only *Haematococcus* species possess is assumed to elevate the stability at lipid environment. Accordingly, for industrial application for astaxanthin by *Haematococcus* species, not only relevant techniques for cell culture in high concentration and for producing astaxanthin in high concentration, but also techniques for recovering the astaxanthin accumulated in a cell with high efficiency must be developed. Particularly, the techniques for culturing photosynthetic microalgae in high concentration have been actively developed through development of photo incubator, etc., but the techniques for separating *Haematococcus* astaxanthin in high concentration have not been actively developed. Therefore, a method of obtaining astaxanthin extract with high purity has not been developed for industrial scale.

A method of recovering the representative *Haematococcus* astaxanthin proposed hitherto includes a mechanical method of extracting astaxanthin by freezing a strain from which water is completely removed with liquid nitrogen, then pulverizing it with an impact mill, and then disrupting the cell wall of the strain; a physical method of extracting astaxanthin with a solvent after disrupting the cell wall of the strain with a machine such as a physical homogenizer; a biological method of extracting astaxanthin after disrupting the cell wall of the strain by employing an enzyme disrupting a cell wall, i.e., cellulase, pectinase, protease, etc. However, these methods have problems of low extraction speed, high disruption rate for astaxanthin, much labor force and high process cost, etc., and thus are not put to practical use. Accordingly, for industrial mass production of astaxanthin employing *Haematococcus* species, there is needed for a new process of separating astaxanthin capable of recovering astaxanthin in high concentration from a strain with high efficiency.

SUMMARY OF THE INVENTION

Therefore, the present invention is directed to provide a method of separating free-astaxanthin selectively by employing two step-two phase solvent extraction process capable of maximizing the separation of free-astaxanthin from a strain for industrial application of *Haematococcus astaxanthin*.

Another object of the present invention is to provide a method of extracting and separating a carotenoid analogue including astaxanthin from a useful microalgae culture containing *Haematococcus* species through the above method.

An exemplary embodiment of the present invention provides a method of separating free-astaxanthin selectively from green microalgae *H. pluvialis* by employing two step-two phase solvent extraction process consisting of alkanic solvent extraction and continuous alcoholic solvent extraction.

In accordance with an exemplary embodiment, the present invention provides a method of separating free-astaxanthin selectively from *Haematococcus pluvialis*, and the method comprises mixing a cell culture containing *Haematococcus pluvialis* with an alkanic solvent and stirring, thereby obtaining an alkanic solvent extract containing astaxanthin material including free-astaxanthin and astaxanthin ester (step 1); and mixing the alkanic solvent extract with an alcohol and stirring, thereby obtaining an alcoholic extract containing free-astaxanthin (step 2).

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
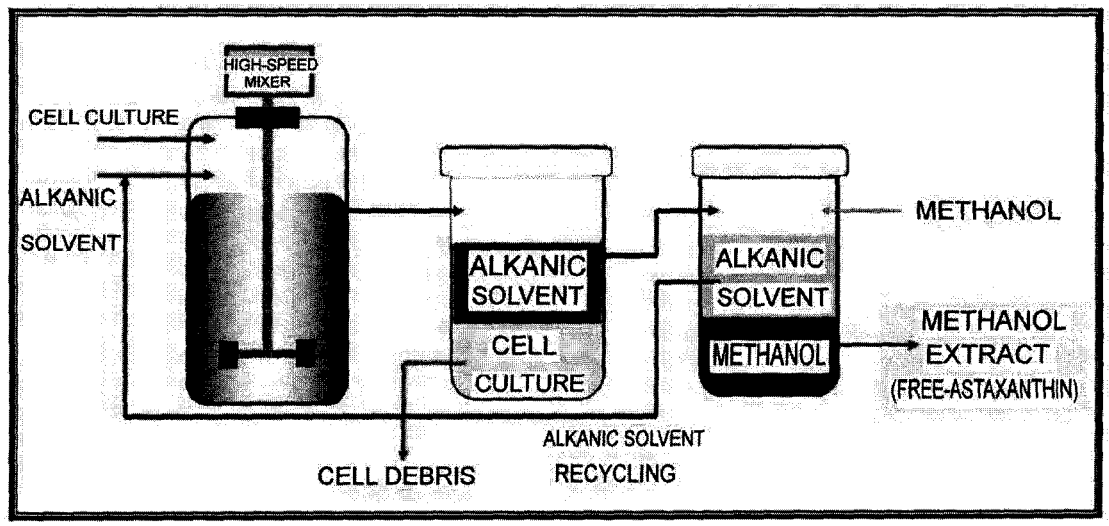
FIG. 1 shows a schematic diagram depicting the two step-two phase solvent extraction process for selective separation of free-astaxanthin used in an embodiment of the present invention.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

In step 1, an alkanic solvent extract containing astaxanthin material is obtained from green microalgae *H. pluvialis*. More particularly, a cell culture is incorporated into the alkanic solvent extraction step, thereby extracting the astaxanthin material within a cell into the alkanic solvent through vigorous mixing with the alkanic solvent.

*H. pluvialis* used in the present invention is a form of a red cyst cell directed to a resting stage, and accumulates high concentration of astaxanthin therein. Astaxanthin accumulated in *H. pluvialis* is generally a mixed form of a free form and an ester form in which fatty acids are connected to terminal groups of the free-astaxanthin by ester bond (linkage), wherein the major fatty acid constituting the ester is $C_{18:1}$ (oleic acid). Accordingly, hydrophobic astaxanthin drained out by cell wall loss is quickly extracted into an alkanic solvent that is a hydrophobic solvent.

The alkanic solvents that can be used in the present invention are all alkanic solvents capable of extracting astaxanthin material. For example, solvents selected from the group consisting of linear or branched $C_1$~$C_{20}$ alkanes can be used, and dodecane can be particularly used. The amount of the alkanic solvent can be controlled according to the concentration of the cell culture, and can be easily controlled without undue experiments to those skilled in the art. Particularly, the cell culture and the alkanic solvent can be used in 1:1 volume ratio.

Further, the alkanic solvent can separate the alkanic solvent extract containing astaxanthin material simply through spontaneous separation by density difference since an alkanic solvent is easily phase-separated from a cell culture.

The step 2 obtains an alcohol extract containing free-astaxanthin by employing an alcohol. More particularly, the alkanic solvent extract separated in the step 1 is mixed with an alcohol solvent in the extraction process of the step 2, and after standing, the astaxanthin material is extracted into the alcoholic solvent.

The alcohols that can be used in the present invention are all alcohols capable of extracting free-astaxanthin material. For example, alcohols selected from the group consisting of linear or branched $C_1$~$C_6$ alcohols can be used, and methanol can be particularly used. The amount of the alcohol can be controlled according to the concentration of the alkanic solvent extract, and can be easily controlled without undue experiments to those skilled in the art. Particularly, the alkanic solvent extract and the alcohol can be used in 1:1 volume ratio.

Meanwhile, a process of converting a highly hydrophobic ester material into a free-astaxanthin form through breaking the ester bond is needed since the highly hydrophobic ester material has a high tendency of remaining in the alkanic solvent. Accordingly, in the present invention, the astaxanthin ester material is induced into the free-astaxanthin form by adding an aqueous solution of sodium hydroxide to the alcohol solvent, thereby hydrolyzing the ester bond at both ends of astaxanthin, and the converted free-astaxanthin is continually extracted into the alcohol solvent. Consequently, the free-astaxanthin is completely extracted into the alcohol solvent, and the free-astaxanthin extract is very easily separated since an alkanic solvent and an alcoholic solvent are spontaneously phase-separated due to their density difference.

Methods of obtaining free-astaxanthin from the alcohol extract thereafter are known to the art, and, for example, free-astaxanthin can be easily obtained by solvent evaporation.

In describing the present invention, spontaneous standing time, extracting time and temperature for phase separation process were not described, since they can be variously controlled depending on the amount and concentration of the cell culture, and those skilled in the art can select them without undue experiments. Therefore, those parameters are not limited to a specific range in the present invention.

Meanwhile, the alkane solvents from which the astaxanthin material is completely extracted hardly comprise the astaxanthin material, and thus are recycled to the extracting process of the step 1 and can be repeatedly used in extracting astaxanthin material from *H. pluvialis* cell culture (FIG. 1).

The method for selective separation according to the present invention can be used in extracting and separating a carotenoid analogue including astaxanthin from not only *Haematococcus pluvialis* but also useful microalgae culture. The specific reaction solvent and reaction condition can vary depending on the specific microalgae, but the extraction process of the step 1 using an alkanic solvent and the extraction process of the step 2 using an alcohol can be performed identically and a desired carotenoid analogue can be easily separated.

The present invention will be described in greater detail with reference to the following examples and the comparative example. However, the following examples are for illustrative purposes only and are not intended to limit the scope of the invention.

Example 1

Selective Separation of Free-Astaxanthin

A well-cultured red *H. pluvialis* cyst cell was subjected to two step-two phase solvent extraction process shown in FIG. 1, thereby separating free-astaxanthin selectively with high efficiency.

(Step 1) A cell culture containing *H. pluvialis* cyst cell and an alkane solvent dodecane were incorporated into the extraction process of the step 1 with 1:1 volume ratio, and then were mixed vigorously. After cell wall loss and extraction of astaxanthin into the dodecane solvent are completed, the mixed solution was standing for a few minutes, and the dodecane extract was spontaneously phase-separated from the cell culture by density difference.

Figure 2:
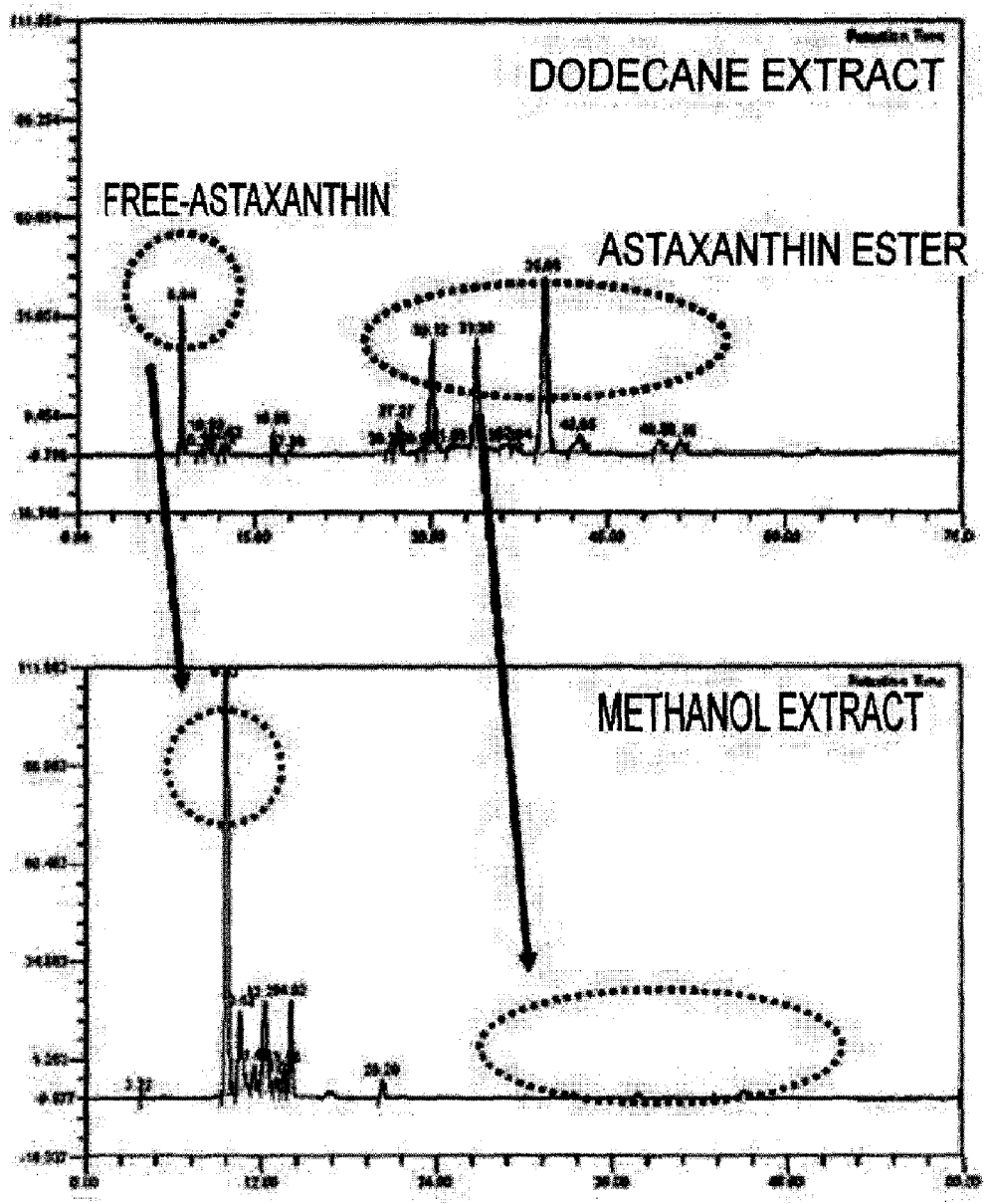
FIG. 2 shows graphs depicting HPLC chromatograms of the dodecane extract of the step 1 and the methanol extract of the step 2 in the two step-two phase solvent extraction process, respectively.

(Step 2) The dodecane extract obtained from the step 1 was incorporated into the extraction process of the step 2, and then was mixed with an alcohol solvent methanol with 1:1 volume ratio. Most of the astaxanthin extract in dodecane had astaxanthin ester form as ascertained in the result of HPLC analysis shown in FIG. 2. Methanol used in the extraction process of step 2 in order to convert various astaxanthin ester material contained in those dodecanes to free-astaxanthin form was a methanol in which 0.02M sodium hydroxide are dissolved. After two phase solvent extraction with dodecane and methanol for a few hours, free-astaxanthin was obtained from the methanol with a recovery rate more than 95% (FIGS. 2 and 3), and the separation of the methanol extract was also performed by spontaneous standing due to density difference as the same as in the dodecane extract.

Comparative Example 1

This example was performed as the same in Example 1 except that pure methanol was used instead of the methanol in which 0.02M sodium hydroxides (NaOH) are dissolved in the extraction process of the step 2.

Figure 3:
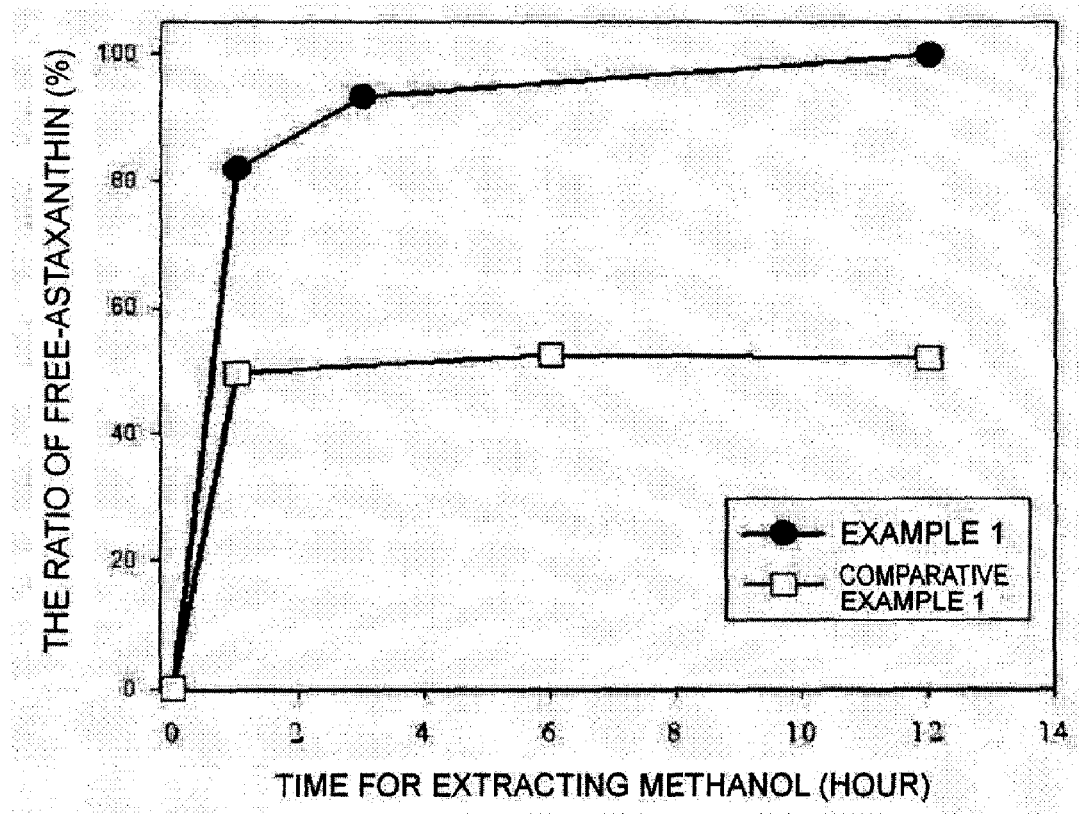
FIG. 3 shows a graph depicting the comparative results of free-astaxanthin extraction when adding sodium hydroxide (Example 1) and when not adding sodium hydroxide (Comparative example 1) in the two step extraction process from *Haematococcus pluvialis* cyst cell into methanol solvent.

The results are shown in FIG. 3 comparing with the results in Example 1. In this comparative example, since hydrolysis reaction by sodium hydroxide did not occur, the conversion of the astaxanthin ester material to free-astaxanthin did not occur. Accordingly, the proportion of free-astaxanthin extracted into methanol was outstandingly low compared to Example 1 as can be seen in FIG. 3.

Example 2

Separation Method Employing the Recycled Dodecane

Since the dodecane from which the astaxanthin material was completely extracted in Example 1 hardly comprised astaxanthin material, the dodecane was recycled to the extraction process of the step 1 and reused in extracting astaxanthin material from *H. pluvialis* cell culture. The process of extracting free-astaxanthin from the dodecane extract was performed as the same as in Example 1, and the results are shown in FIG. 4.

Figure 4:
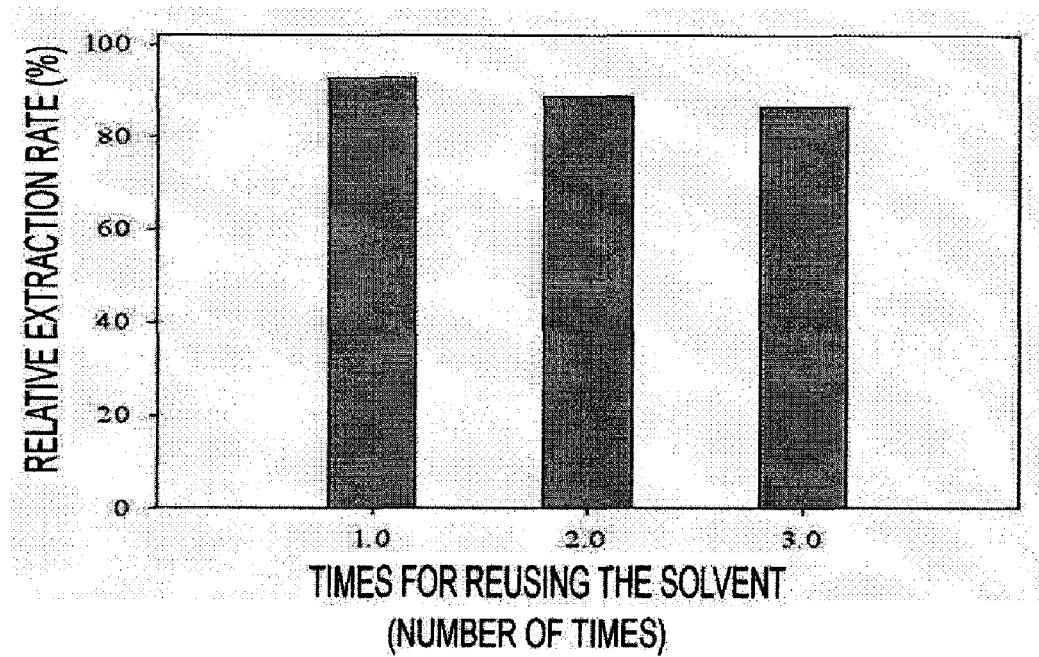
FIG. 4 shows a graph depicting the results of the extraction rate for free-astaxanthin by reuse of the dodecane solvent as an extracting solvent in the step 1.

As shown in FIG. 4, even though the dodecane solvent was recycled and reused 3 times, the recovery rate of astaxanthin was more than 80% compared to that in case of using new dodecane solvent.

As described in the above, the present invention can not only maximize the efficiency of separating astaxanthin in high concentration by providing a very simple process technique capable of recovering free-astaxanthin selectively from *H. pluvialis* culture with high efficiency, but also realize the economical and simple operation of the process of separating free-astaxanthin by repeatedly using an alkanic solvent as a mediating solvent for extracting free-astaxanthin.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

What is claimed is:

1. A method of separating free-astaxanthin selectively from *Haematococcus pluvialis*, the method comprising:
    mixing a cell culture containing *Haematococcus pluvialis* with a dodecane solvent with 1:1 volume ratio and stirring, thereby obtaining a dodecane solvent extract containing astaxanthin material including free-astaxanthin and astaxanthin ester (step 1);
    mixing the dodecane solvent extract with a methanol with 1:1 volume ratio, wherein an aqueous solution of sodium hydroxide is added to the methanol, and stirring, thereby obtaining a methanol extract containing free-astaxanthin and separating the dodecane solvent from the methanol extract (step 2); and
    recycling the dodecane solvent separated from the alcoholic extract in the step 2 by carrying out the step 1 and the step 2 repeatedly (step 3).

2. The method according to claim 1, wherein the dodecane solvent extract is obtained by phase separation from the cell culture through spontaneous standing by density difference between the dodecane solvent and the cell culture in the step 1, and the methanol extract containing free-astaxanthin is obtained by phase separation from the dodecane solvent through spontaneous standing by density difference between the dodecane solvent and the methanol in the step 2.

* * * * *